United States Patent
Trainoff

(10) Patent No.: US 7,331,218 B2
(45) Date of Patent: Feb. 19, 2008

(54) CAPILLARY BRIDGE VISCOMETER AND METHOD FOR MEASURING SPECIFIC VISCOSITY

(75) Inventor: Steven Trainoff, Goleta, CA (US)

(73) Assignee: Wyatt Technology Corporation, Santa Barbara, CA (US)

( * ) Notice: Subject to any disclaimer, the term of this patent is extended or adjusted under 35 U.S.C. 154(b) by 62 days.

(21) Appl. No.: 11/233,644

(22) Filed: Sep. 23, 2005

(65) Prior Publication Data
US 2007/0068229 A1    Mar. 29, 2007

(51) Int. Cl.
*G01N 11/08*    (2006.01)
(52) U.S. Cl. ..................... 73/54.06; 73/54.05
(58) Field of Classification Search ............... 73/54.04, 73/54.05, 54.06, 54.07, 54.09
See application file for complete search history.

(56) References Cited

U.S. PATENT DOCUMENTS

| | | | | |
|---|---|---|---|---|
| 2,449,067 A | * | 9/1948 | Guillemin, Jr. | 73/23.21 |
| 3,086,386 A | * | 4/1963 | Kapff | 73/23.2 |
| 3,808,877 A | * | 5/1974 | Blair | 73/54.06 |
| 4,384,472 A | * | 5/1983 | Tournier | 73/30.01 |
| 4,463,598 A | * | 8/1984 | Haney | 73/54.06 |

OTHER PUBLICATIONS

Waters, J. et al., "Characterization of Hyaluronic Acid with On-Line Differential Viscometry, Multiangle Light Scattering, and Differential Refractometry," LCGC North America, Mar. 2005, pp. 302-306.*
van der Heyden, F.H.J. et al., "A Low Hydraulic Capacitance Pressure Sensor for Integration with a Micro Viscosity Detector," Sensors and Actuators B, vol. 92, 2003, pp. 102-109.*
Blom, M.T. et al., "A Differential Viscosity Detector for Use in Miniaturized Chemical Separation Systems," Journal of Microelectromechanical Systems, vol. 14, No. 1, Feb. 2005, pp. 70-80.*
Haney, M.A., "The Differential Viscometer. II. On-Line Viscosity Detector for Size-Exclusion Chromatography," Journal of Applied Polymer Science, vol. 30, 1985, pp. 3037-3049.*
Wyatt Technology Corporation Brochure: ViscoStar Viscometer, Jun. 4, 2004.*

* cited by examiner

*Primary Examiner*—Daniel S. Larkin
(74) *Attorney, Agent, or Firm*—John R. Thompson; Stoel Rives LLP

(57) ABSTRACT

A bridge viscometer for measuring specific viscosity, $\eta_{sp}(t)$, includes four capillaries, a delay volume, and a pressure transducer. The pressure transducer generates a signal indicative of a pressure differential, $\Delta p(t)$, as a sample is introduced into the bridge viscometer. The specific viscosity, $\eta_{sp}(t)$, of the sample is calculated based on the pressure differential, $\Delta p(t)$, and a predetermined internal pressure, $IP_0$.

20 Claims, 2 Drawing Sheets

CAPILLARY BRIDGE VISCOMETER AND METHOD FOR MEASURING SPECIFIC VISCOSITY

TECHNICAL FIELD

The field relates generally to viscometers and viscosity measurement methods.

BRIEF DESCRIPTION OF THE DRAWINGS

Various embodiments of the invention are now described with reference to the figures, in which.

DETAILED DESCRIPTION

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the apparatus, system, and method of the present invention, as represented in FIGS. 1 and 2, is not intended to limit the scope of the invention, as claimed, but is merely representative of presently preferred embodiments of the invention.

Parts of the description will be presented in terms of operations performed through the execution of programming instructions. As well understood by those skilled in the art, these operations often take the form of electrical, magnetic, or optical signals capable of being stored, transferred, combined, and otherwise manipulated through, for instance, electrical components. Various operations will be described as multiple discrete steps performed in turn in a manner that is helpful in understanding the present invention. However, the order of description should not be construed as to imply that these operations are necessarily performed in the order they are presented, or even order dependent.

Embodiments of the invention may be represented as a software code resident on a computer readable medium (also referred to as a machine-accessible medium, computer-accessible medium, or a processor-accessible medium). The computer readable medium may be any type of magnetic, optical, or electrical storage medium including a diskette, CD-ROM, memory device (volatile or non-volatile), or similar storage mechanism. The computer readable medium may contain various sets of instructions, code sequences, configuration information, or other data. Those of ordinary skill in the art will appreciate that other instructions and operations necessary to implement the described invention may also be stored on the computer readable medium.

Figure 1:
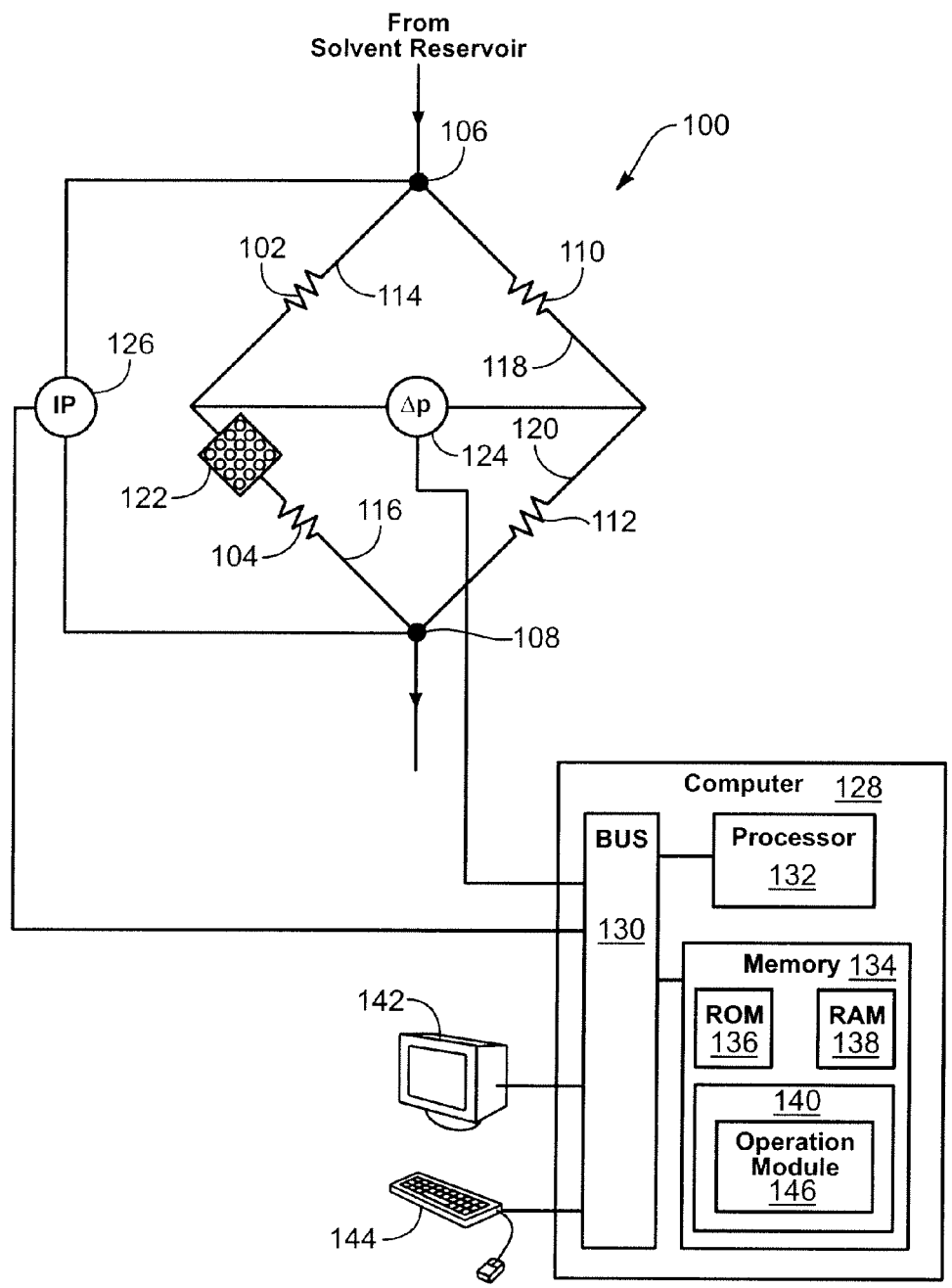
FIG. 1 is a block diagram illustrating a bridge viscometer.
Figure 2:
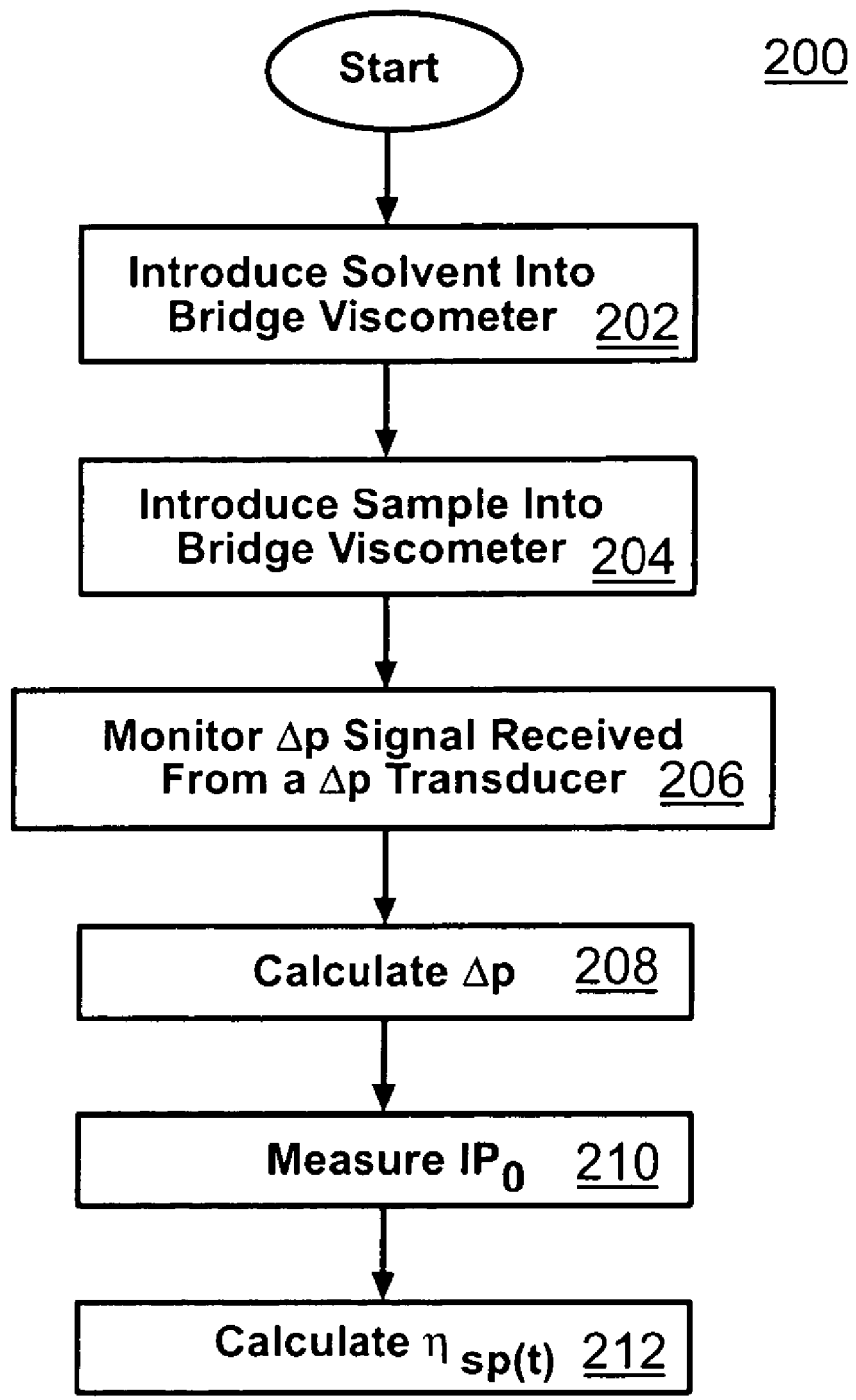
FIG. 2 is a flow diagram illustrating a method for determining specific viscosity of a sample.

Referring to FIG. 1, a schematic illustrates an embodiment of a capillary bridge viscometer 100. A bridge viscometer accurately measures specific viscosity of a solute in a suitable solvent. The specific viscosity is defined as $\eta_{sp} = \eta/\eta_0 - 1$, where $\eta$ is the viscosity of the sample, $\eta_0$ is the viscosity of the solvent. A bridge viscometer is useful in determining the molecular parameters of a polymer including molar mass and hydrodynamic radius. One such bridge viscometer suitable for use as described herein is the ViscoStar™ viscometer manufactured by Wyatt Technology Corporation of Santa Barbara.

The bridge viscometer 100 includes first and second capillaries 102 and 104 that are in series communication between supply and discharge ports 106 and 108. The bridge viscometer 100 further includes third and fourth capillaries 110 and 112 that are in series communication between the supply and discharge ports 106 and 108. The capillaries 102, 104 and 110, 112 are in parallel communication with one another between the supply and discharge ports 106 and 108 to form a fluid analog of well known Wheatstone (i.e., resistance) bridge in the electrical art. Each capillary 102, 104, 110, and 112, is coupled to a corresponding fluid arm 114, 116, 118, and 120 to provide fluid communication.

A delay volume 122 is disposed in the fluid arm 116 and in series between capillaries 102 and 104. The delay volume 122 is constructed so to have a negligible flow impedance, but an internal volume significantly greater than the fluid arm 116.

A differential pressure ($\Delta p$) transducer 124 is coupled to fluid arms 114, 116, 118, and 120 to measure the $\Delta p$ across the bridge viscometer 100 when different fluids are flowing through the capillaries 102, 104, 110, 112 thereof. An inlet pressure (IP) transducer 126 is coupled to the supply and discharge ports 106 and 108 to measure the pressure from the inlet to the outlet of the bridge viscometer 100. Typically, a zero reading of the $\Delta p$ transducer 124 provides an indication that the bridge viscometer 100 is in balance. The bridge viscometer 100 is balanced to achieve accurate test results and a wide dynamic range.

The bridge viscometer 100 may include a computer system 128 in electrical communication with the $\Delta p$ and IP transducers 124 and 126. It will be apparent to those of ordinary skill in the art that a variety of computer system architectures may be employed. The computer system 128 may include a bus 130 for communicating information and a processor 132 coupled with the bus 130 for processing information. The bus architecture employed by computer system 128 may be a shared bus architecture.

The processor 132 may be any of a wide variety of general-purpose or specific-purpose processors, microprocessors, or micro-controllers, such as processors manufactured by Intel® Corporation. A memory 134 is in electrical communication with the bus 130 for storing data and executable instructions for the processor 132. The memory 134 may include a read-only memory 136 for storing static information and instructions for the processor 132. The memory 134 may include a random access memory 138 for short-term storage. The memory 134 may further include a storage device 140 for non-volatile, long-term memory storage. The storage device 140 may include a conventional hard disk drive, floppy disk drive, CD-ROM drive, or other magnetic or optical data storage device for reading and writing information stored on a hard disk, a floppy disk, a CD-ROM a magnetic tape, or other magnetic or optical data storage medium.

A display device 142 is in electrical communication with the bus 130 for displaying information for a user. The display device 142 may be a liquid crystal device, cathode ray tube (CRT), or other suitable display device. The computer system 128 includes an input device 144 in electrical communication with the bus 130 for communicating information and command selections to the processor 132. The input device 144 may include a keyboard and a pointing device, such as a conventional mouse or trackball device.

The processor 132 retrieves processing instructions from an operation module 146 that is resident, in whole or in part, within memory 134. The operation module 146 directs the processor 132 to gather pressure data from the Δp and IP transducers 124 and 126 and execute calculations based on the pressure data in accordance with the present invention. Command selections and information input at input device 144 may be used to direct the flow of instructions executed by processor 132. The results of processed execution may be displayed on the display device 142.

In operation, a solvent is supplied from a solvent reservoir to the supply port 106 by a pump, such as a low pulsation chromatography pump. As the solvent propagates through the bridge viscometer, the Δp transducer 124 reads zero. After the solvent is present throughout the bridge viscometer 100, a sample is introduced into the supply port 106. The sample splits evenly between arms 114 and 118. When the sample enters the delay volume 122, three capillaries 102, 110, and 112 contain sample, and the capillary 104 contains only solvent. This creates a pressure imbalance within the bridge viscometer 100 that is detected by Δp transducer 124. The sample specific viscosity, $\eta_{sp}$, can be determined from the combination of the Δp imbalance and the inlet pressure as a function of time through the relation:

$$\eta_{sp}(t) = \frac{4\Delta p(t)}{IP(t) - 2\Delta p(t)}. \tag{1}$$

However, this assumes that the transducers 124 and 126 have ideal performance and are perfectly linear and that their frequency responses are identical. In particular, a pump system produces pulses at a specific frequency. The bridge viscometer 100 sensitivity is limited by the pressure amplitude of the pump pulses. Increased baseline noise leads to a lower signal-to-noise (S/N) and thus lowered experimental accuracy. By using elaborate pulse dampeners, pump pulses can be reduced but, unfortunately, not eliminated. If the Δp and IP transducers 124 and 126 have different phase shifts at the drive frequency, then the ratio in Eq. (1) may not properly divide out the pulses. In this case, it is advantageous to use only the Δp(t) signal to compute $\eta_{sp}(t)$.

The fundamental observation is that the IP and Δp signals are not independent measurements. In particular, the IP transducer 126 by itself effectively acts as a single capillary viscometer so that one may write:

$$IP(t) = IP_0 \frac{\eta(t)}{\eta_0} = IP_0(\eta_{sp} + 1), \tag{2}$$

where $IP_0$ is the pressure measured by the IP transducer 126 when pure solvent is passing through the bridge viscometer. Thus, $IP_0$ does not depend on measurements from a sample. $IP_0$ can be accurately measured by time averaging a section of solvent baseline so that any pump pulses average to zero. Here $\eta_0$ is the viscosity of the solvent, and $\eta(t)$ is the viscosity of the sample as a function of time. Inserting Eq. (2) into Eq. (1) gives the equation:

$$\eta_{sp}(t) = \frac{4\Delta p(t)}{IP_0(\eta_{sp}(t) + 1) - 2\Delta p(t)}, \tag{3}$$

which can be rearranged for the quadratic equation for $\eta_{sp}(t)$, $$\eta_{sp}(t)^2 IP_0 + \eta_{sp}(t)(IP_0 - 2\Delta p(t)) - 4\Delta p(t) = 0. \tag{4}$$

This can be solved for $\eta_{sp}(t)$ as:

$$\eta_{sp}(t) = \frac{\Delta p(t)}{IP_0} + \frac{1}{2}\left(\sqrt{1 + 12\frac{\Delta p(t)}{IP_0} + 4\frac{\Delta p(t)^2}{IP_0^2}} - 1\right). \tag{5}$$

The positive root of the quadratic equation is chosen since the negative root is unphysical.

$IP_0$ can either be measured before or after the sample is introduced to the bridge. The quantity $IP_0$ can be computed as:

$$IP_0 = R\eta_0 f \tag{6}$$

where R is the flow impedance of the bridge, $\eta_0$ is the solvent viscosity, and f is the flow rate. The flow impedance R is a value that can theoretically be considered a constant. During manufacture, the bridge viscometer may be calibrated and $IP_0$ may be calculated and stored in memory 134. The IP transducer 126 may be removed as IP(t) is not needed during operation of a bridge viscometer. Alternatively, if the IP transducer 126 is retained, $IP_0$ can be measured by averaging the IP transducer while pure solvent is flowing through the bridge. The latter method is preferred since R may drift over time, and recalibration may otherwise be required.

Referring to FIG. 2, a flow diagram is shown to illustrate a method 200 to determine specific viscosity. The operation module 146 may perform the method 200 in whole or in part. The operation module 146 may be implemented as a computer program product that may include a computer readable medium having stored thereon instructions that may be used to program the computer system 128, or other electronic device, to perform a process. A computer readable medium may include, but is not limited to, optical disks, CD-ROMs, DVD, floppy diskettes, magneto-optical disks, ROMs, RAMs, EPROMs, EEPROMs, magnet or optical cards, propagation media or other type of media/machine readable mediums suitable for storing electronic instructions. For example, the operation module 146 may be downloaded as a computer program product, wherein the program may be transferred from a remote computer to a requesting or client computer by way of data signals embodied in a carrier wave or other propagation medium via a communication link.

A solvent is introduced 202 into a bridge viscometer until all four capillaries are filled with solvent and the transducers 124, 126 have stabilized. A sample is introduced 204 into the bridge viscometer until three of the four capillaries include the sample. The delay volume 122 delays the sample into the fourth capillary. A Δp signal is monitored 206 from the Δp transducer 124. Based on the Δp signal, Δp(t) is calculated 208. $IP_0$ is measured 210 by averaging the IP transducer signal, $$IP_0 < IP(t) > \tag{7}$$

or $IP_0$ may be computed from a previously stored flow impedance, the known flow rate, and the known solvent viscosity. As previously discussed, $IP_0$ may be measured before or after a sample is introduced. $\eta_{sp}(t)$ is calculated 212 from Δp(t) and $IP_0$ as recited in equation (5). As can be appreciated, the recited method 200 is only one example for illustrative purposes, and alternative embodiments and variations are within the scope of the invention.

A methodology described herein utilizes only the average pressure of an IP transducer signal when solvent is in the bridge and the time dependent signal measured from the $\Delta p(t)$ signal. A lower quality IP transducer may be used as IP values are averaged and not time dependent. This simplifies the data gathering, allows use of legacy instruments, and potentially reduces the contaminating effects of pump pulses.

Embodiments of the present invention include various steps which have been described above. The steps may be embodied in machine-executable instructions that may be used to cause a general purpose or special purpose processor to perform the steps. Alternatively, these steps may be performed by specific hardware components that contain hardwired logic for performing the steps, or by any combination of programmed computer components and custom hardware components.

While specific embodiments and applications of the present invention have been illustrated and described, it is to be understood that the invention is not limited to the precise configuration and components disclosed herein. Various modifications, changes, and variations apparent to those of skill in the art may be made in the arrangement, operation, and details of the methods and systems of the present invention disclosed herein without departing from the spirit and scope of the present invention.

What is claimed is:

1. A method for determining a specific viscosity, $\eta_{sp}(t)$, of a sample introduced into a bridge viscometer having four capillaries and a delay volume, comprising:
   determining an internal constant pressure value, $IP_0$, of pure solvent passing through the bridge viscometer;
   receiving a pressure transducer signal indicative of a pressure differential, $\Delta p(t)$, upon introduction of the sample into three of the four capillaries; and
   calculating $\eta_{sp}(t)$ based on a relationship of $\Delta p(t)$ and $IP_0$.

2. The method of claim 1, wherein calculating $\eta_{sp}(t)$ includes the relationship, $$\eta_{sp}(t) = \frac{\Delta p(t)}{IP_0} + \frac{1}{2}\left(\sqrt{1 + 12\frac{\Delta p(t)}{IP_0} + 4\frac{\Delta p(t)^2}{IP_0^2}} - 1\right).$$

3. The method of claim 1, wherein determining an internal pressure value, $IP_0$, includes time averaging IP signals received from an IP transducer in communication with the bridge viscometer.

4. The method of claim 1, wherein determining an internal pressure value, $IP_0$, includes calculating the relationship, $IP_0 = R\eta_0 f,$ where R is the flow impedance of the bridge, $\eta_0$ is a solvent viscosity, and f is the flow rate.

5. The method of claim 1, further comprising introducing a solvent into the four capillaries prior to introduction of the sample into three of the four capillaries.

6. A computer readable medium having stored thereon computer instruction code for performing a method for determining a specific viscosity, $\eta_{sp}(t)$, of a sample introduced into a bridge viscometer having four capillaries and a delay volume, the method comprising:
   determining an internal constant pressure value, $IP_0$, of pure solvent passing through the bridge viscometer;
   receiving a pressure transducer signal indicative of a pressure differential, $\Delta p(t)$, upon introduction of the sample into three of the four capillaries; and
   calculating $\eta_{sp}(t)$ based on a relationship of $\Delta p(t)$ and $IP_0$.

7. The computer readable medium of claim 6, wherein calculating $\eta_{sp}(t)$ includes the relationship, $$\eta_{sp}(t) = \frac{\Delta p(t)}{IP_0} + \frac{1}{2}\left(\sqrt{1 + 12\frac{\Delta p(t)}{IP_0} + 4\frac{\Delta p(t)^2}{IP_0^2}} - 1\right).$$

8. The computer readable medium of claim 6, wherein determining an internal pressure value, $IP_0$, includes time averaging IP signals received from an IP transducer in communication with the bridge viscometer.

9. The computer readable medium of claim 6, wherein determining an internal pressure value, $IP_0$, includes calculating the relationship, $IP_0 = R\eta_0 f,$ where R is the flow impedance of the bridge, $\eta_0$ is a solvent viscosity, and f is the flow rate.

10. The computer readable medium of claim 6, wherein the method further comprises identifying that a solvent is introduced into the four capillaries prior to introduction of the sample into three of the four capillaries.

11. A computer system, comprising:
   a processor; and
   a memory in electrical communication with the processor and having stored thereon computer readable instruction code, including an operational module for performing a method for determining a specific viscosity, $\eta_{sp}(t)$, of a sample introduced into a bridge viscometer having four capillaries and a delay volume, the method including:
      receiving a pressure transducer signal indicative of a pressure differential, $\Delta p(t)$, upon introduction of the sample into three of the four capillaries;
      determining an internal constant pressure value, $IP_0$, of pure solvent passing through the bridge viscometer; and
      calculating $\eta_{sp}(t)$ based on a relationship of $\Delta p(t)$ and $IP_0$.

12. The computer system of claim 11, wherein calculating $\eta_{sp}(t)$ includes the relationship, $$\eta_{sp}(t) = \frac{\Delta p(t)}{IP_0} + \frac{1}{2}\left(\sqrt{1 + 12\frac{\Delta p(t)}{IP_0} + 4\frac{\Delta p(t)^2}{IP_0^2}} - 1\right).$$

13. The computer system of claim 11, wherein determining an internal pressure value, $IP_0$, includes time averaging IP signals received from an IP transducer in communication with the bridge viscometer.

14. The computer system of claim 11, wherein determining an internal pressure value, $IP_0$, includes calculating the relationship, $IP_0 = R\eta_0 f,$ where R is the flow impedance of the bridge, $\eta_0$, is a solvent viscosity, and f is the flow rate.

15. The computer system of claim 11, wherein the method further comprises identifying that a solvent is introduced into the four capillaries prior to introduction of the sample into three of the four capillaries.

16. A bridge viscometer to determine a specific viscosity $\eta_{sp}(t)$ of a sample, comprising:
- first and second capillaries disposed in series communication;
- third and fourth capillaries disposed in series communication and in parallel to the first and second capillaries;
- a delay volume disposed in series communication between the first and second capillaries;
- a pressure transducer, in communication with the capillaries, to determine a differential pressure, $\Delta p(t)$;
- a processor in electrical communication with the pressure transducer; and
- a memory in electrical communication with the processor and having stored thereon computer readable instruction code for performing a method for determining a specific viscosity, $\eta_{sp}(t)$, of an introduced sample, the method including:
  - receiving a pressure transducer signal indicative of a pressure differential, $\Delta p(t)$, upon introduction of the sample into three of the four capillaries;
  - determining an internal constant pressure value, $IP_0$, of pure solvent passing through the bridge viscometer; and
  - calculating $\eta_{sp}(t)$ based on a relationship of $\Delta p(t)$ and $IP_0$.

17. The bridge viscometer of claim 16 wherein calculating $\eta_{sp}(t)$ includes the relationship, $$\eta_{sp}(t) = \frac{\Delta p(t)}{IP_0} + \frac{1}{2}\left(\sqrt{1 + 12\frac{\Delta p(t)}{IP_0} + 4\frac{\Delta p(t)^2}{IP_0^2}} - 1\right).$$

18. The bridge viscometer of claim 16, further comprising:
- an IP transducer, in communication with the capillaries, to determine $IP_0$, and
- wherein determining an internal pressure, $IP_0$, includes time averaging IP signals received from an IP transducer in communication with the bridge viscometer.

19. The bridge viscometer of claim 16, wherein determining an internal pressure value, $IP_0$, includes calculating the relationship, $$IP_0 = R\eta_0 f,$$

where R is the flow impedance of the bridge, $\eta_0$ is a solvent viscosity, and f is the flow rate.

20. The bridge viscometer of claim 16, wherein the method further comprises identifying that a solvent is introduced into the four capillaries prior to introduction of the sample into three of the four capillaries.

* * * * *

UNITED STATES PATENT AND TRADEMARK OFFICE
CERTIFICATE OF CORRECTION

PATENT NO. : 7,331,218 B2  Page 1 of 1
APPLICATION NO. : 11/233644
DATED : February 19, 2008
INVENTOR(S) : Steven Trainoff It is certified that error appears in the above-identified patent and that said Letters Patent is hereby corrected as shown below:

Column 4, Line 60, Figure 7 reads, "$IP_0 < IP(t) >$" which should read --$IP_0 = < IP(t) >$--

Signed and Sealed this

Twenty-fourth Day of June, 2008

JON W. DUDAS
*Director of the United States Patent and Trademark Office*